United States Patent
Miller et al.

(10) Patent No.: US 10,925,482 B2
(45) Date of Patent: Feb. 23, 2021

(54) SYSTEMS AND METHODS FOR MEASURING POSTLENS TEAR FILM THICKNESS

(71) Applicant: LUTRONIC VISION INC., Burlington, MA (US)

(72) Inventors: Seth Adrian Miller, Longmont, CO (US); Mark Meloni, Longmont, CO (US)

(73) Assignee: LUTRONIC VISION INC, Burlington, MA (US)

( * ) Notice: Subject to any disclaimer, the term of this patent is extended or adjusted under 35 U.S.C. 154(b) by 0 days.

(21) Appl. No.: 16/954,219

(22) PCT Filed: Jun. 15, 2018

(86) PCT No.: PCT/US2018/037791
§ 371 (c)(1),
(2) Date: Jun. 16, 2020

(87) PCT Pub. No.: WO2019/133043
PCT Pub. Date: Jul. 4, 2019

(65) Prior Publication Data
US 2020/0329960 A1    Oct. 22, 2020

Related U.S. Application Data

(63) Continuation-in-part of application No. PCT/US2017/068977, filed on Dec. 29, 2017.

(51) Int. Cl.
*A61B 3/10* (2006.01)
*G01B 11/06* (2006.01)

(52) U.S. Cl.
CPC .............. *A61B 3/101* (2013.01); *A61B 3/102* (2013.01); *G01B 11/0675* (2013.01)

(58) Field of Classification Search
CPC ......... A61B 3/0025; A61B 3/14; A61B 3/101; A61B 3/1005; A61B 3/0058; A61B 3/10;
(Continued)

(56) References Cited

U.S. PATENT DOCUMENTS

| 4,747,683 A | 5/1988 | Doane |
| 6,236,459 B1 | 5/2001 | Negahdaripour et al. |

(Continued)

OTHER PUBLICATIONS

International Search Report and Written Opinion for International Application No. PCT/US2017/068977 dated May 4, 2018, pp. 10.
(Continued)

*Primary Examiner* — Brandi N Thomas

(57) ABSTRACT

A dosimetry system may comprise a film stack and a laser system for applying a laser beam to the film stack. The system may further comprise an interferometry system configured to acquire from the film stack a first interferometric dataset comprising a first composite signal and a subsequent interferometric dataset comprising a subsequent composite signal. The system may also include a processor for comparing the first and subsequent composite signals, wherein a difference between the first and subsequent composite signals indicates a change in the film stack thickness. A dosimetry method may comprise applying a laser beam to such a film stack, acquiring the first and subsequent interferometric datasets, comparing them to detect a change in the film stack thickness, and ceasing to apply the laser beam to the film stack if the change in the film stack thickness exceeds a predetermined threshold.

20 Claims, 6 Drawing Sheets

(58) Field of Classification Search
CPC ....... A61B 3/0041; A61B 3/1241; A61B 3/16; A61B 3/185; A61B 3/107; A61B 3/0008; A61B 3/113; A61B 3/112; A61B 3/102; A61B 3/156; A61B 5/01; A61B 5/1455; A61B 5/14555; A61B 5/14507; A61B 5/0002; A61B 5/14532; A61B 5/031; A61B 5/14539; A61B 5/14546; A61B 5/1486; A61B 5/18; A61B 5/412; A61B 5/416; A61B 5/445; A61B 5/4839; A61B 5/6814; A61B 5/6821; A61B 5/1103; A61B 5/742; A61B 5/0015; A61B 5/0496; A61B 5/1477; A61B 5/7246; A61B 5/746; A61B 5/053; A61B 5/0537; A61B 2560/0214; A61B 2560/0219; A61B 2560/0252; A61B 2560/0418; A61B 2562/0238; A61B 2562/12; A61B 2560/0475; A61B 2562/0219; A61B 2562/02; A61B 8/06; A61B 8/56; A61B 18/12; A61B 2017/00084; A61B 2018/046; A61B 2018/048; A61F 9/0017; A61F 9/0026; A61F 9/00; A61F 9/0079; A61F 9/008; A61F 9/00772; A61F 2/1624; A61F 2/16; A61F 2250/0002; A61F 2009/00844; A61F 2009/00857; A61F 2009/00872; A61F 2007/0004; A61F 2007/0059; A61F 7/007; A61F 7/12; G06T 2207/30041; G06T 7/0012
See application file for complete search history.

(56) References Cited

U.S. PATENT DOCUMENTS

| | | |
|---|---|---|
| 2008/0273171 A1 | 11/2008 | Huth et al. |
| 2011/0237999 A1 | 9/2011 | Muller et al. |
| 2014/0240671 A1* | 8/2014 | Korb ..................... A61B 3/101 351/206 |
| 2015/0351628 A1 | 12/2015 | Huth et al. |
| 2017/0216090 A1 | 8/2017 | Kim |
| 2017/0266041 A1 | 9/2017 | Kim et al. |

OTHER PUBLICATIONS

International Search Report and Written Opinion for International Application No. PCT/US2018/037791 dated Sep. 12, 2018, pp. 6.

* cited by examiner

SYSTEMS AND METHODS FOR MEASURING POSTLENS TEAR FILM THICKNESS

CROSS-REFERENCE TO RELATED APPLICATIONS

The present application is a U.S. National Stage filing under 35 U.S.C. § 371 of International Application PCT/US2018/037791, filed Jun. 15, 2018 and entitled "Systems And Methods For Measuring Postlens Tear Film Thickness," which claims priority to and benefit of PCT Application Serial No. PCT/US2017/068977, filed Dec. 29, 2017, entitled "Systems and Methods for Measuring Postlens Tear Film Thickness." The International Applications, including any appendices or attachments thereof, are hereby incorporated herein by reference in their entirety.

BACKGROUND

Laser photocoagulation is used to treat or slow the progression of a number of eye diseases. During laser treatment, a contact lens is placed on the eye, forming a film between the contact lens and the eye. Laser treatment can create one or more water vapor bubbles within the eye, which create a pressure wave that ultimately influences the thickness of the film. If the creation of a single bubble can be detected, laser treatment can be stopped before an area of the eye receives too much energy and is likely to be damaged. Measuring the thickness of the film is one way to detect bubble formation, but current methods require analysis of a number of different signals from different areas of the eye in order to determine the thickness of the film, making quick and accurate detection of film thickness change difficult.

SUMMARY

In some embodiments, a method comprises placing a contact lens on an eye, thereby forming a film stack having a thickness, the film stack comprising the contact lens, a postlens tear film, and the eye. In some embodiments, the method further comprises acquiring a first interferometric dataset from the film stack, wherein the first interferometric dataset comprises a first composite signal, and acquiring a subsequent interferometric dataset from the film stack, wherein the subsequent interferometric dataset comprises a subsequent composite signal. In some embodiments, the method still further comprises comparing the first composite signal to the subsequent composite signal, wherein a difference between the first composite signal and the subsequent composite signal indicates a change in the thickness of the film stack.

In some embodiments, a dosimetry system comprises a film stack and a laser system configured to apply at least one laser beam to a portion of the film stack. In some embodiments, the dosimetry system further comprises an interferometry system configured to acquire from the film stack a first interferometric dataset comprising a first composite signal and a subsequent interferometric dataset comprising a subsequent composite signal. In some embodiments, the dosimetry system still further comprises a processor configured to compare the first composite signal and the subsequent composite signal, wherein a difference between the first composite signal and the subsequent composite signal indicates a change in the thickness of the film stack.

In some embodiments, a dosimetry method comprises applying at least one laser beam to a film stack. In some embodiments, the dosimetry method further comprises acquiring a first interferometric dataset from the film stack while the at least one laser beam is applied, wherein the first interferometric dataset comprises a first composite signal. In some embodiments, the dosimetry method still further comprises acquiring a subsequent interferometric dataset from the film stack while the at least one laser beam is applied, wherein the subsequent interferometric dataset comprises a subsequent composite signal. In some embodiments, the dosimetry method also includes comparing the first composite signal to the subsequent composite signal, wherein a difference between the first composite signal and the subsequent composite signal indicates a change in the thickness of the film stack. In some embodiments, the dosimetry method further includes ceasing to apply the at least one laser beam to the film stack if the change in thickness of the film stack exceeds a predetermined threshold.

DETAILED DESCRIPTION

Figure 1:
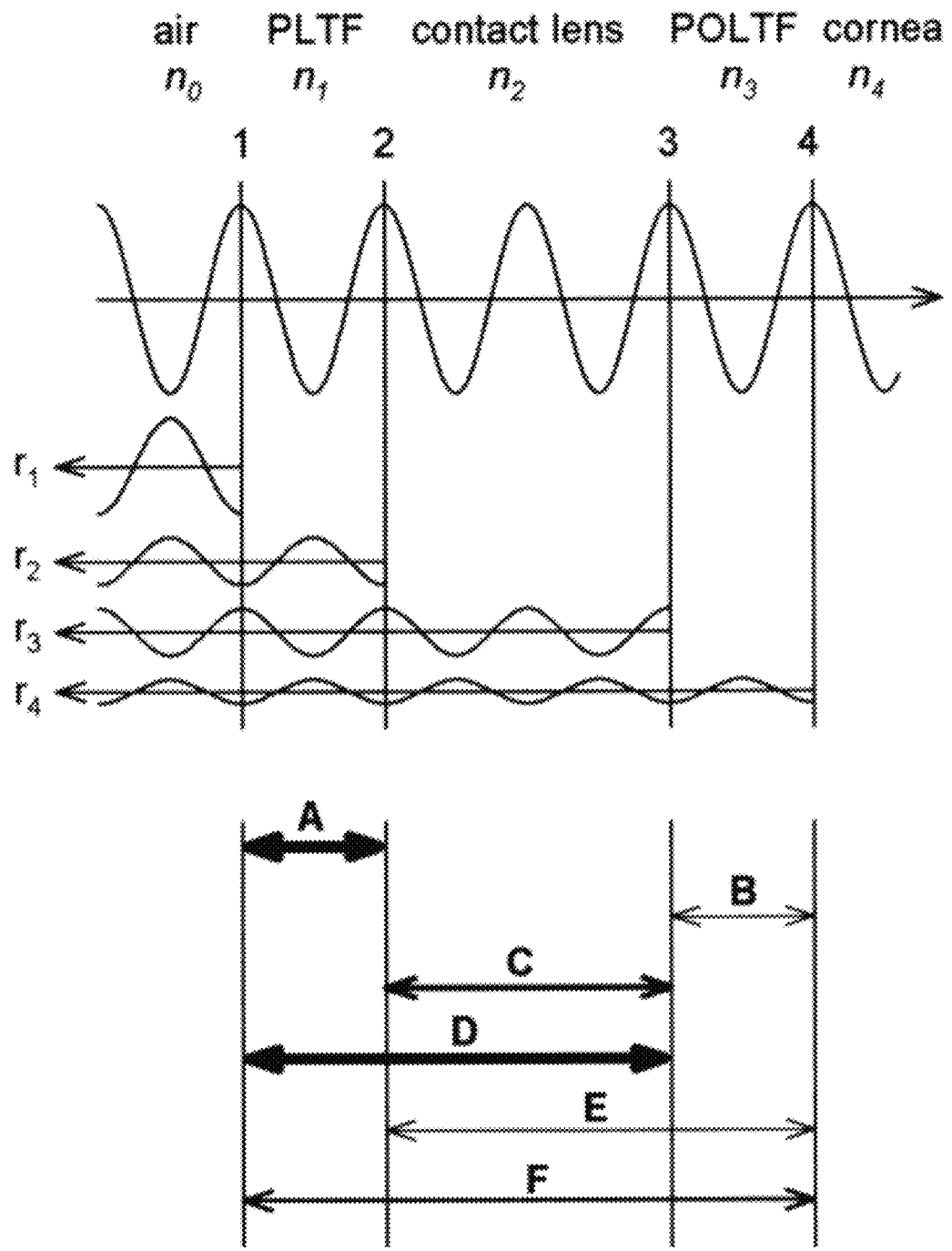
FIG. 1 illustrates a prior art multilayer system comprising a number of individual signals for measuring tear film thickness, which differs from the methods and systems described herein.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

As used herein, the term "composite" means including a number of elements capable of being separated through processing or other methods. A "composite signal," then, refers to a signal that includes a number of signals from different components of a substrate, where the signals are capable of being separated through processing or other methods, but if they are not separated they form a signal that includes, or is a sum of, the separable signals. A "composite signal," for example, may describe an interferometric signal from a film stack, where the composite signal includes a number of signals from different substrates or components within the film stack, but when taken as a whole the composite signal includes, or is the sum of, the separable signals from the different substrates of the film stack.

The Use of Laser Eye Treatment

The retinal pigment epithelium (RPE) is a single layer of pigmented hexagonal cells that supports photoreceptor cells within an eye, and is essential for proper retinal function. The RPE is located just outside the neurosensory retina, which nourishes retinal visual cells, and is firmly attached to the underlying choroid and overlying retinal visual cells. The RPE is one of a number of areas of the eye that may receive laser treatment in a variety of situations and pathologies.

Laser photocoagulation of the RPE is a form of selective retinal laser therapy (SRT) and is used to treat or slow the progression of a number of eye diseases, including age-related macular degeneration (AMD), proliferative retinopathy, macular edema, central serous retinopathy, and extrafoveal subretinal neovascular membranes. A number of different laser systems may be used for this type of laser treatment, including any commercially available laser systems. One such laser system used for this type of treatment is the R:GEN Laser System, a product of Lutronic, Inc.

The eye naturally has a film over its surface. During laser treatment of the eye, a contact lens is placed on the eye. The contact lens is squeezed to the eye by capillary pressure, which depends on the match in curvature of the contact lens to the eye and the intraocular pressure (i.e., the "tightness" of the fit of the contact lens against the eye). A "postlens tear film" (i.e., a layer or film between the contact lens and the eye) forms to cushion the interface between the contact lens and the surface of the eye (usually the cornea). Changes in the local pressures near the postlens tear film can impact the thickness of that film. If the contact lens is a "good fit" for the eye, the lens will be adhered to the eye with a pressure of about 0.02 psi, and the postlens tear film will be relatively thin. In contrast, if the contact lens is a "poor fit" for the eye, the lens will be adhered more weakly, and thus will have a thicker postlens tear film. The average thickness of a tear film is about 4.5 μm, with a normal range from about 2 μm to about 8 μm. A postlens tear film formed by a contact lens having a "poor fit" may have a thickness of up to about 100 μm in some instances. The thickness of a tear film may be, for example, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, or any range between any two of these values, including endpoints.

Laser treatment of the eye can create one or more micron-sized water vapor bubbles at the RPE layer. The intensity of a laser beam is not homogeneous, so it is possible for one cell within the eye to receive a high dose of energy, which creates a single bubble, while other cells may not receive enough energy to create any bubbles. If one area of the RPE layer receives a very high dose of energy from the laser beam, which can result in overheating and subsequent cellular damage, a number of bubbles may be created in that area. If the creation of a single bubble can be detected, laser treatment can be stopped before an area of the RPE layer receives too much energy and is likely to be damaged.

When bubbles are created within the eye, an acoustic pressure wave arises from them. The acoustic pressure wave is directed toward the contact lens, and will alternately compress and expand the postlens tear film by displacing its boundaries. This compression and expansion of the postlens tear film will occur for both "good" and "poor" contact lens fits, because the tear film pressure is not sufficient to resist deformation from the acoustic pressure wave. If the thickness of the postlens tear film is carefully monitored, the creation of a single bubble may be detected. In other words, monitoring the thickness of the postlens tear film during laser treatment can be an effective form of dosimetry during laser treatment of the eye.

Bubbles during this type of treatment have previously been measured using optical reflectometry, which is a non-contact method for measuring the scattering of laser light, where an increase in signal amplitude indicates bubble formation. Bubbles have also previously been measured using acoustic pressure measurements, which measure the pressure wave that occurs when the bubble is formed, and are currently captured by a sensor embedded into the contact lens, where a shift of the resulting data curve indicates bubble formation. The embedded sensor is often a piezoelectric sensor. These types of optical reflectometry and acoustic pressure measurements both have low sensitivity, and are unable to distinguish changes due to bubble formation from changes due to simple heating.

Furthermore, the piezoelectric sensor used in acoustic pressure measurements is difficult to embed into a contact lens, and doing so necessarily creates a new interface (i.e., the transducer-lens interface). This new interface can result in a loss of signal (i.e., a reduction in the signal-to-noise ratio). Piezoelectric sensors are manually embedded into lenses, which increases costs and may lead to significant part-to-part variability. Thus, there exists a need for a system and method capable of measuring the acoustic pressure wave that results from bubble formation during laser treatment of the eye that has an improved signal-to-noise ratio, does not require manual assembly or custom parts, and is more cost effective than the existing sensor system that many laser treatment systems, including any commercially available laser treatment system such as the R:GEN Laser System, currently employ.

The systems and methods described herein include an interferometric technique for measuring the thickness of the postlens tear film in real time or near-real time during laser surgical treatment of the eye. Any interferometric technique or system may be used in the systems and methods described herein. One such interferometric technique is optical coherence tomography (OCT). OCT is an established medical imaging technique that uses light to capture micron-resolution three-dimensional (3D) images of tissue. OCT is based on low-coherence interferometry, and typically employs near-infrared light. The light's relatively long wavelength allows it to penetrate the tissue or film stack (i.e., the "scattering medium"). OCT can be used to probe the entire film stack, thereby measuring the response of reflected light to the incident acoustic pressure wave in real time or near-real time.

The concept of measuring the thickness of an optically transparent film in real time to detect a photoacoustic signal has previously been demonstrated: an optical device referred to as the FP Etalon (i.e., a Fabry-Perot sensor) uses a compliant transparent film coated between two reflecting surfaces and measures the distance between those surfaces using interferometry. In the systems and methods described herein, the postlens tear film is effectively a Fabry-Perot sensor: it is a transparent film sandwiched between two substrates of different refractive indices, making it possible for interferometry to be performed.

Interferometry is known for its high precision, with the capability to measure changes in thickness of less than an Angstrom. Interferometry and OCT (which relies upon interferometry to capture its images) have been used to determine the thickness of the postlens tear film under static conditions. In those cases, the precision of the measurement was on the order of tens of nanometers across multiple measurements at different times, despite the highly dynamic nature of the eye.

Figure 2:
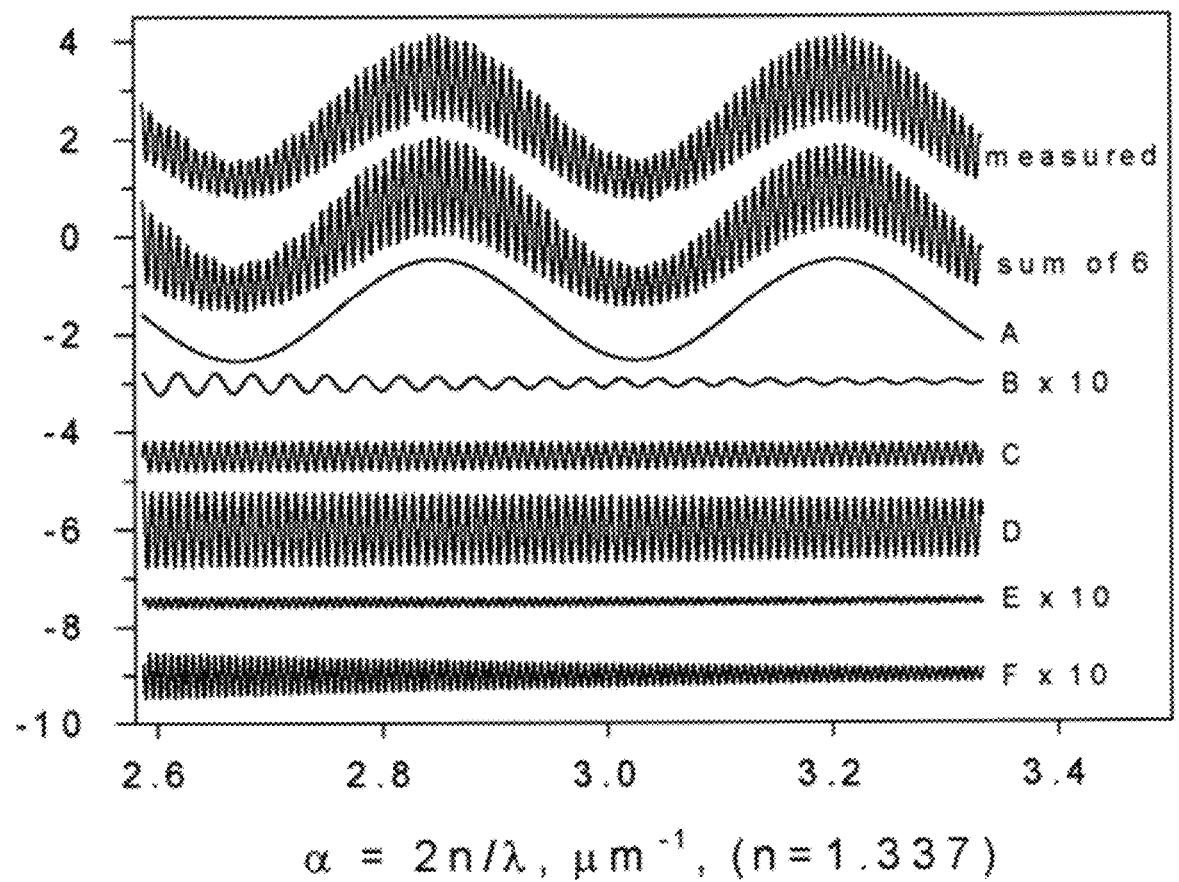
FIG. 2 illustrates an alternative prior art multilayer system comprising a number of individual signals for measuring tear film thickness, which differs from the methods and systems described herein.
Figure 3:
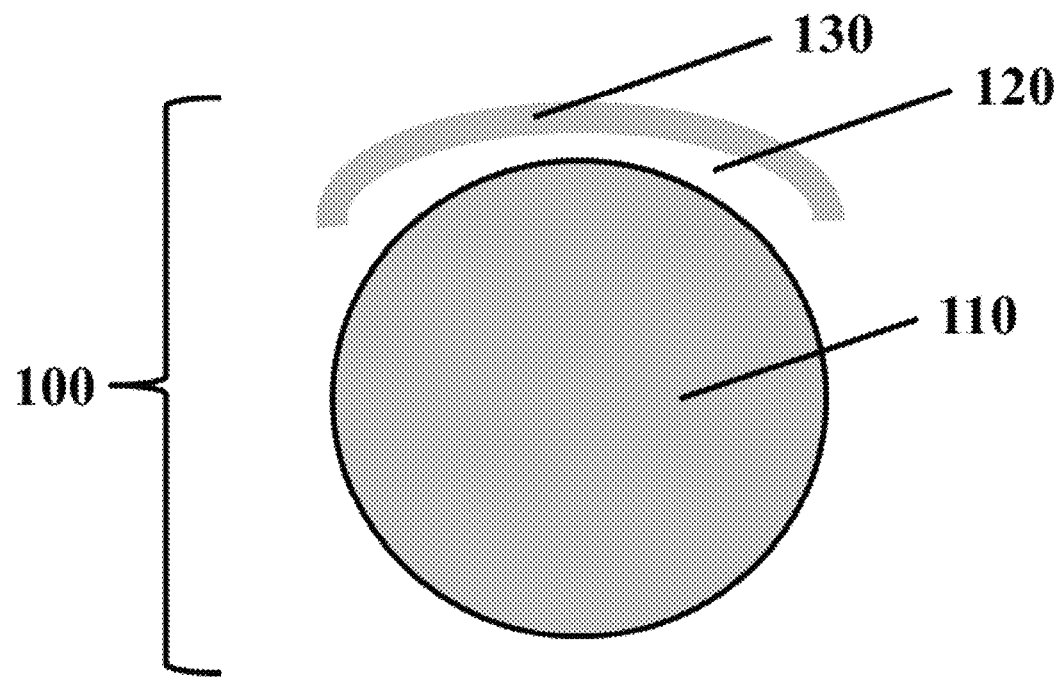
FIG. 3 is a schematic illustration of an embodiment of a film stack comprising an eye, a contact lens, and a postlens tear film, in accordance with the present disclosure.

Using interferometry for laser dosimetry in the eye, as described herein, has the distinct advantage of requiring only relative (i.e., not absolute) composite interferometric signals. This concept contrasts with previously described multilayer systems that either acquire a number of individual signals and add them, or acquire a single signal and filter them to determine the relevant individual signals for measuring tear film thickness. Examples of such multilayer systems are illustrated in FIG. 1 and FIG. 2. The methods and systems described herein use an unfiltered, unprocessed composite signal to measure tear film thickness. In other words, the exact thickness of the postlens tear film does not need to be determined; only the degree of change in the thickness is. During the high-speed measurements described herein, which take place over tens of microseconds, it is unnecessary to worry about processes such as evaporation of water from the surface of the eye, because those processes are relatively slow, and their resulting low frequency can easily be filtered. The remaining high-frequency signal will like all interferometric probing, be exquisitely sensitive to small changes in postlens tear film thickness.

Using interferometry as described herein instead of the above-described methods previously employed will reduce cost, complexity, and variability. In addition, where OCT is used, signal-to-noise ratio will be improved because optical measurements are the most sensitive type available. Further, interferometry, and specifically OCT, is backwards-compatible with existing laser treatment systems, whether private or commercially available, including the R:GEN Laser System, and future hardware plans for an interferometry-integrated laser treatment systems can be used without significant changes.

Dosimetry Methods

Figure 5:
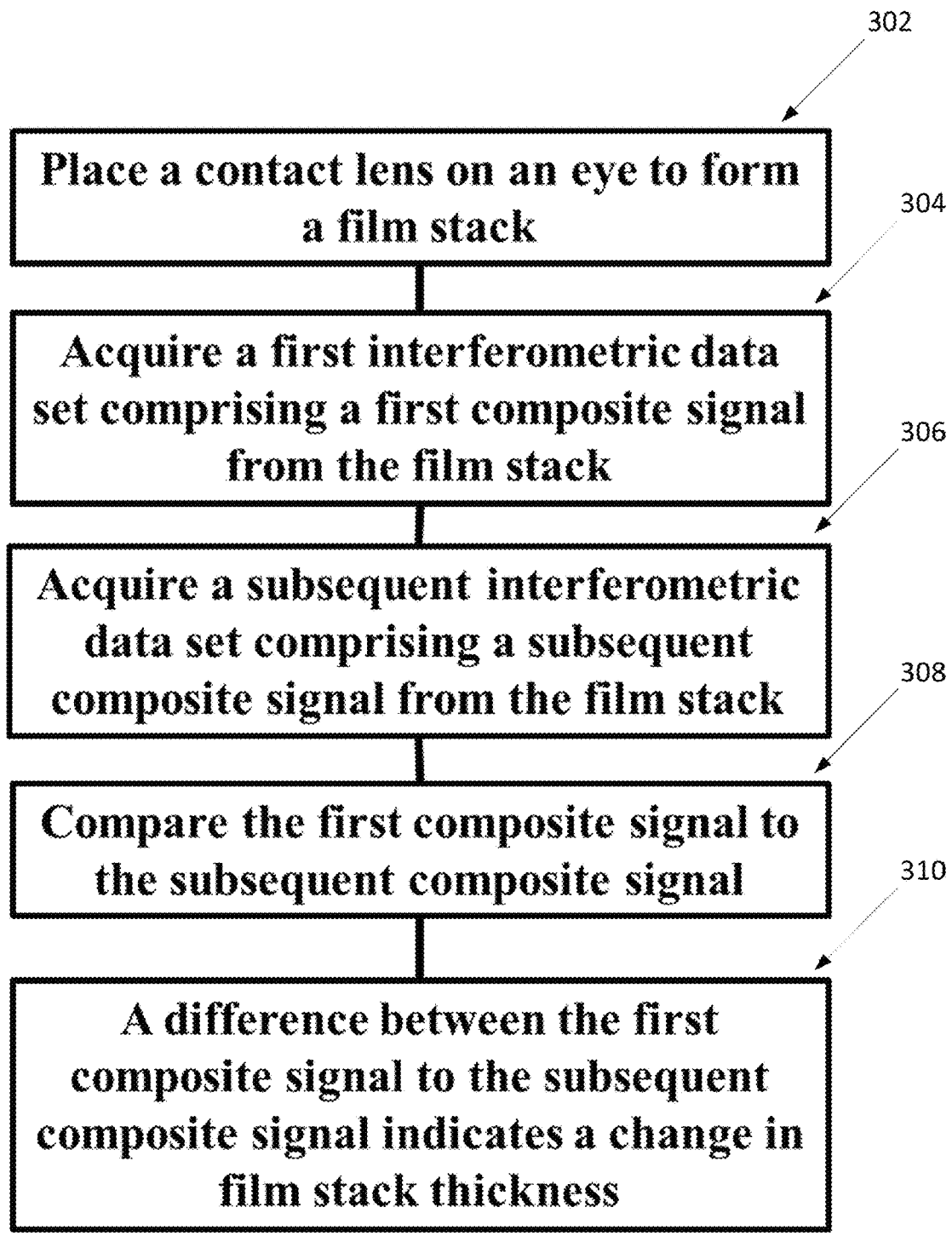
FIG. 5 is a flow chart showing the steps of an embodiment of a method as described herein.

In some embodiments as shown in FIG. 5, a method may comprise placing a contact lens on an eye, thereby forming a film stack 302. The method may further comprise acquiring a first interferometric dataset from the film stack 304. In some embodiments, the first interferometric dataset may comprise tomographic images. In some embodiments, the first interferometric dataset may comprise optical coherence tomographic (OCT) images. In certain embodiments, the first interferometric dataset may comprise a first composite signal. In some embodiments, the first composite signal may be a single signal from the film stack as a whole. In some embodiments, the first interferometric dataset may be acquired without physically contacting the film stack or any portion or component thereof.

The film stack 100 may have a thickness. In certain embodiments, the thickness of the film stack may be from about 25 mm to about 30 mm. The thickness of the film stack may be, for example, about 25 mm, about 26 mm, about 27 mm, about 28 mm, about 29 mm, about 30 mm, or any range between any two of these values, including endpoints. The postlens tear film 120 may also have a thickness, as described above.

In some embodiments, a method may further comprise acquiring a first interferometric dataset from the film stack 306. In some embodiments, the first interferometric dataset may comprise tomographic images. In some embodiments, the first interferometric dataset may comprise optical coherence tomographic (OCT) images. In certain embodiments, the tomographic images may comprise a 3-D structural data set. In some embodiments, the tomographic images may comprise a 4-D structural data set. In one embodiment, the 4-D structural data set may comprise any one of an A, B, C, and/or M OCT scan. In certain embodiments, the first interferometric dataset may comprise a first composite signal. In some embodiments, the first composite signal may be a single signal from the film stack as a whole. In some embodiments, the first interferometric dataset may be acquired without physically contacting the film stack or any portion or component thereof.

In some embodiments, a method may further comprise acquiring a subsequent interferometric dataset from the film stack. In some embodiments, the subsequent interferometric dataset may comprise tomographic images. In some embodiments, the subsequent interferometric dataset may comprise optical coherence tomographic (OCT) images. In certain embodiments, the tomographic images may comprise a 3-D structural data set. In some embodiments, the tomographic images may comprise a 4-D structural data set. In one embodiment, the 4-D structural data set may comprise any one of an A, B, C, and/or M OCT scan. In certain embodiments, the subsequent interferometric dataset may comprise a subsequent composite signal. In some embodiments, the subsequent composite signal may be a single signal from the film stack as a whole. In some embodiments, the subsequent interferometric dataset may be acquired without physically contacting the film stack or any portion or component thereof.

In some embodiments, a method may still further include comparing the first composite signal to the subsequent composite signal 308, wherein a difference between the first composite signal and the subsequent composite signal indicates a change in the thickness of the film stack 310. In such embodiments, the comparing may be accomplished by applying a single bin Fast Fourier Transform (FFT) to each of the first composite signal and the subsequent composite signal. The comparing may be accomplished without separating the composite signal into its individual components for further analysis.

The comparing may be done over a period from about 1 millisecond (ms) to about 900 ms. The comparing may be done over a period of, for example, about 1 ms, about 5 ms, about 10 ms, about 20 ms, about 25 ms, about 50 ms, about 100 ms, about 150 ms, about 200 ms, about 250 ms, about 300 ms, about 350 ms, about 400 ms, about 450 ms, about 500 ms, about 550 ms, about 600 ms, about 650 ms, about 700 ms, about 750 ms, about 800 ms, about 850 ms, about 900 ms, or any range between any two of these values, including endpoints. In certain embodiments, the comparing may be done in real time. In other embodiments, the comparing may be done in near-real time.

In certain embodiments, the change in thickness of the film stack, as determined by comparing the first composite signal to the subsequent composite signal, may correlate with a change in the thickness of the postlens tear film. In some embodiments, the change in thickness of the film stack may be approximately equal to the change in thickness of the postlens tear film. Without wishing to be bound by theory, the rapid nature with which the first composite signal and the subsequent composite signal are acquired and compared may allow for the change in the thickness of the film stack, as determined by comparing the first and subsequent composite signals, to be due to, or substantially due to, the change in the thickness of the postlens tear film, perhaps because the postlens tear film is the only substrate within the film stack that may change as dynamically as the composite signals are acquired. As described herein, a change in the postlens tear film thickness may be due to the formation of bubbles at the RPE layer during laser treatment of the eye. In other words, a change in the thickness of the film stack may correspond with the formation of bubbles at the RPE of the eye.

In certain embodiments, acquiring the subsequent interferometric dataset comprises acquiring a plurality of subsequent interferometric datasets over a period of time, wherein each of the subsequent interferometric datasets independently comprises a subsequent composite signal. In such embodiments, comparing the first composite signal to the subsequent composite signal may comprise comparing the first composite signal to each of the plurality of subsequent composite signals. In other embodiments, comparing the first composite signal to the subsequent composite signal may further comprise comparing an earlier-acquired subsequent composite signal to a later-acquired composite signal, in the same manner in which the first composite signal was compared to the earliest-acquired subsequent composite signal. In some embodiments, the subsequent interferometric datasets may be acquired throughout the course of laser treatment of the eye, such that the comparing step to determine a change in the thickness of the film stack may be used throughout the course of laser treatment to monitor the formation of bubbles within the eye.

In certain embodiments, both the first interferometric dataset and the subsequent interferometric dataset may be acquired while one or more laser beams are applied to the film stack. In some such embodiments, the laser beams may be applied to the film stack using a laser treatment system. In some embodiments, the laser treatment system is an R:GEN Laser System. In certain embodiments, the laser treatment system may comprise any commercially available laser treatment system. In some embodiments, the laser treatment system may comprise any laser treatment system.

In some embodiments, the method may further comprise ceasing the laser treatment to the film stack if the change in the thickness of the film stack exceeds a predetermined threshold. In certain embodiments, the predetermined threshold may be associated with a level or amount of bubble formation within the eye during laser treatment that may be associated with damage to the eye. In such embodiments, the step of ceasing the laser treatment if the change in the thickness of the film stack exceeds a predetermined threshold may protect the eye from damage. In certain embodiments, the predetermined threshold may be from about 5 nm to about 50 nm. In some embodiments, the predetermined threshold may be from about 3 nm to about 100 nm. The predetermined threshold may be, for example, about 3 nm, about 4 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, or any range between any two of these values, including endpoints. In other embodiments, the physician, healthcare provider, or technician administering the treatment may set the predetermined threshold in accordance with a patient's individual needs and anatomy. The predetermined threshold may be configured to prevent damage to the eye, or any of its tissues or structures, caused by overheating.

In some embodiments, a dosimetry method may comprise applying at least one laser beam to a film stack, as described herein. In certain embodiments, applying the at least one laser beam may comprise applying a series of laser beams. In some embodiments, applying the at least one laser beam may be done using a laser treatment system as described herein.

Figure 6:
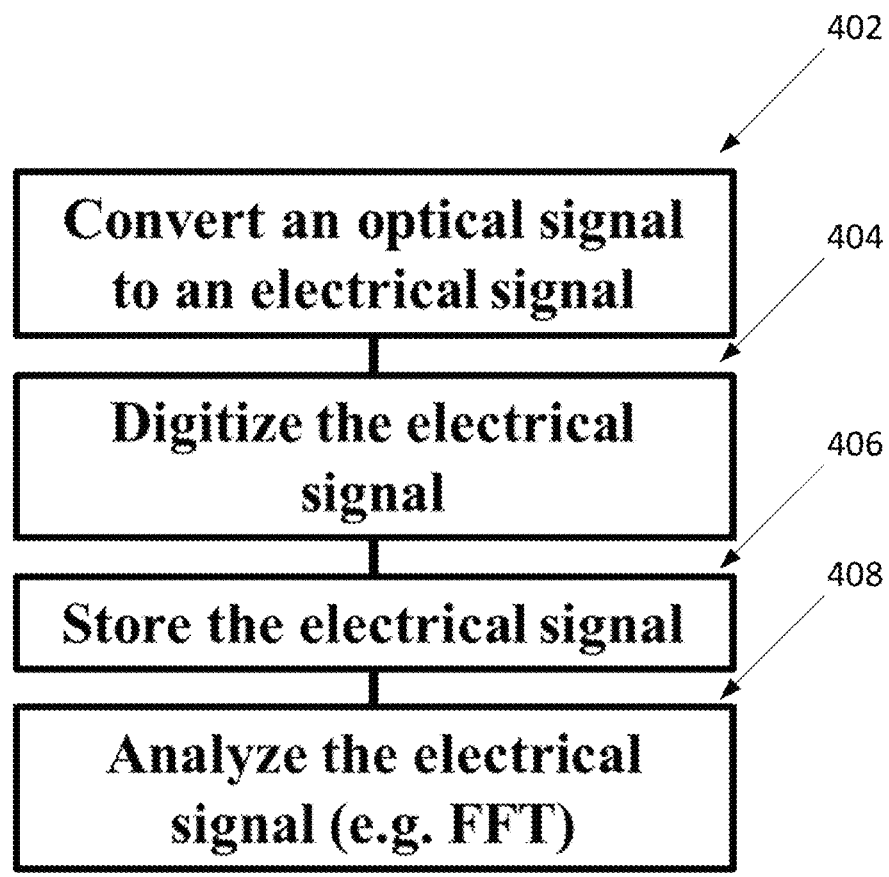
FIG. 6 is a flow chart further describing the steps involved in acquiring a first interferometric data set and acquiring a subsequent interferometric data set in an embodiment of a method as described in FIG. 5.

The dosimetry method may further comprise acquiring a first interferometric dataset from the film stack while the at least one laser beam is applied, wherein the first interferometric dataset comprises a first composite signal, as described herein. The dosimetry method may still further comprise acquiring a subsequent interferometric dataset from the film stack while the at least one laser beam is applied, wherein the subsequent interferometric dataset comprises a subsequent composite signal, as described herein. The dosimetry method may also comprise comparing the first composite signal to the subsequent composite signal, wherein a difference between the first composite signal and the subsequent composite signal indicates a change in the thickness of the film stack, as described herein. The dosimetry method may further comprise ceasing to apply the at least one laser beam to the film stack if the change in thickness of the film stack exceeds a predetermined threshold, as described herein. FIG. 5 is a flow chart showing the steps of an embodiment of a method as described herein. FIG. 6 is a flow chart further describing the steps involved in acquiring a first interferometric data set and acquiring a subsequent interferometric data set in an embodiment of a method as described in FIG. 5. As shown in FIG. 6, an optical signal may be converted to an electrical signal 402, the electrical signal may be digitized 404, the electrical signal may be stored 406, and the electrical signal may be analyzed 408, for example through FFT.

Dosimetry Systems

A dosimetry system may comprise a film stack, as described herein. A dosimetry system may further comprise a laser system configured to apply at least one laser beam to a portion of the film stack, or to the entire film stack, as described herein.

The dosimetry system may also comprise an interferometry system configured to acquire from the film stack a first interferometric dataset comprising a first composite signal and a subsequent interferometric dataset comprising a subsequent composite signal, as described herein. The interferometry system may comprise any system configured to acquire interferometric data. In certain embodiments, the interferometric system may comprise a tomographic imaging system. In certain embodiments, the tomographic imaging system may produce a 3-D structural data set. In some embodiments, the tomographic imaging system may produce a 4-D structural data set. In one embodiment, the 4-D structural data set may comprise any one of an A, B, C, and/or M OCT scan. In some embodiments, the interferometric system may comprise an optical coherence tomographic (OCT) imaging system.

The dosimetry system may further comprise a processor 202 configured to compare the first composite signal and the subsequent composite signal, wherein a difference between the first composite signal and the subsequent composite signal indicates a change in the thickness of the film stack 216, as described herein. The processor may reside within or outside of a computer system, and may be configured to compare the first and subsequent composite signals in accordance with the present disclosure. In some embodiments, the processor may be configured to accomplish the comparing by applying a single bin Fast Fourier Transform (FFT) to each of the first composite signal and the subsequent composite signal. In other embodiments, the processor may be configured to accomplish the comparing by applying any other transform known in the art that can be accomplished in near-real time with the given parameters, as described herein.

Figure 4:
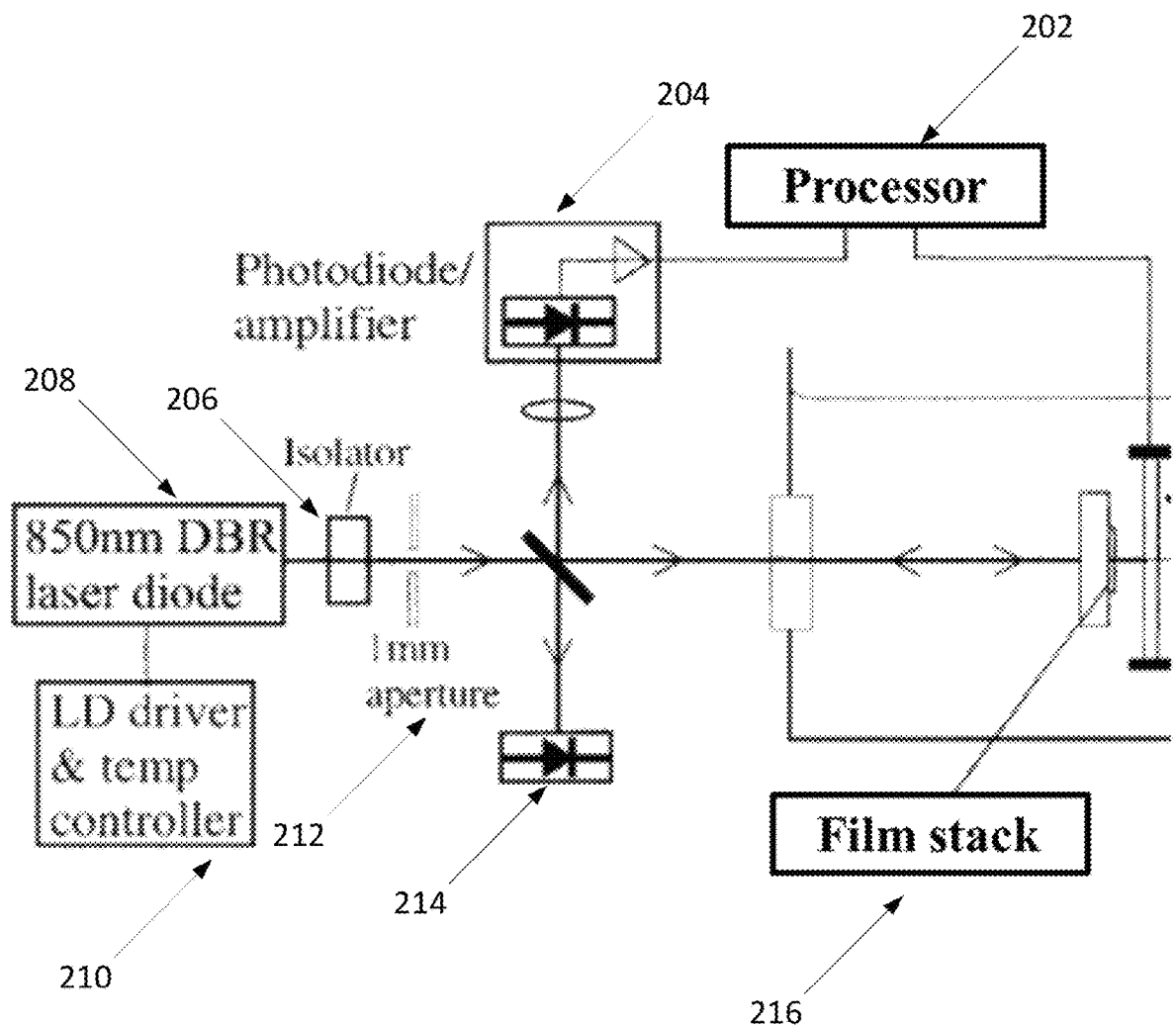
FIG. 4 is a schematic illustration of an embodiment of a dosimetry system as described herein.

The various embodiments of such a dosimetry system include the various embodiments of the film stack, the application of a laser beam to the film stack, and the acquiring and comparing of the first and subsequent composite signals, in accordance with the present disclosure. FIG. 4 is a schematic illustration of an embodiment of a dosimetry system as described herein. The dosimetry system may also include a photodiode/amplifier 204, an isolator 206, a laser diode 208 e.g., 850 nm DBR), an LD driver and temperature controller 210, a 1 mm aperture 212, a photodiode 214, in addition to the processor 202 and film stack 216.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art, from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation, no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general, such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general, such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in tennis of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 signals refers to groups having 1, 2, or 3 signals. Similarly, a group having 1-5 signals refers to groups having 1, 2, 3, 4, or 5 signals, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method comprising:
placing a contact lens on an eye, thereby forming a film stack having a thickness, wherein the film stack comprises the contact lens, a postlens tear film, and the eye;
acquiring a first interferometric dataset from the film stack, wherein the first interferometric dataset comprises a first composite signal;
acquiring a subsequent interferometric dataset from the film stack, wherein the subsequent interferometric dataset comprises a subsequent composite signal;
comparing the first composite signal to the subsequent composite signal; and
determining a change in the thickness of the film stack based on the comparison, wherein a difference between the first composite signal and the subsequent composite signal indicates the change in the thickness of the film stack, and the change in the thickness of the film stack corresponds to a formation of bubbles at a retinal pigment epithelium of the eye.

2. The method of claim 1, wherein the change in the thickness of the film stack further correlates with a change in the postlens tear film.

3. The method of claim 1, wherein comparing the first composite signal to the subsequent composite signal comprises applying a single bin Fast Fourier Transform to each of the first composite signal and the subsequent composite signal.

4. The method of claim 1, wherein acquiring the subsequent interferometric dataset comprises acquiring a plurality of subsequent interferometric datasets over a period of time, and wherein each of the subsequent interferometric datasets independently comprises a subsequent composite signal.

5. The method of claim 4, wherein comparing the first composite signal to the subsequent composite signal comprises comparing the first composite signal to each of the plurality of subsequent composite signals.

6. The method of claim 1, further comprising:
applying a laser treatment to the film stack, wherein acquiring the first interferometric dataset and acquiring the subsequent interferometric dataset occur while applying the laser treatment to the film stack.

7. The method of claim 6, further comprising ceasing the laser treatment to the film stack if the change in the thickness of the film stack exceeds a predetermined threshold.

8. The method of claim 7, wherein the predetermined threshold is from about 3 nm to about 100 nm.

9. A dosimetry system comprising:
a contact lens configured to be placed on an eye, wherein the contact lens forms a portion of a film stack further comprising the eye and a tear film;
a laser system configured to apply at least one laser beam to a portion of the film stack;
an interferometry system configured to acquire from the film stack a first interferometric dataset comprising a first composite signal and a subsequent interferometric dataset comprising a subsequent composite signal; and
a processor configured to:
compare the first composite signal and the subsequent composite signal: and
determine a change in the thickness of the film stack based on the comparison, wherein a difference between the first composite signal and the subsequent composite signal indicates the change in the thickness of the film stack, and the change in the thickness of the film stack corresponds to a formation of bubbles at a retinal pigment epithelium of the eye.

10. The dosimetry system of claim 9, wherein the change in the thickness of the film stack further correlates with a change in the tear film.

11. The dosimetry system of claim 9, wherein the processor is configured to compare the first composite signal and the subsequent composite signal in near-real time.

12. The dosimetry system of claim 9, wherein the subsequent interferometric dataset comprises acquiring a plurality of subsequent interferometric datasets over a period of time, and wherein each of the subsequent interferometric datasets independently comprises a subsequent composite signal.

13. The dosimetry system of claim 12, wherein the processor is configured to compare the first composite signal to each of the plurality of subsequent composite signals.

14. The dosimetry system of claim 9, wherein the interferometry system is configured to acquire from the film stack the first interferometric dataset and the second interferometric dataset while the laser system is applying at least one laser beam to the portion of the film stack.

15. The dosimetry system of claim 9, wherein the interferometry system is one of a tomographic imaging system and an optical coherence tomographic imaging system.

16. A dosimetry method comprising:
applying at least one laser beam to a film stack comprising an eye and a tear film;
acquiring a first interferometric dataset from the film stack while the at least one laser beam is applied, wherein the first interferometric dataset comprises a first composite signal;
acquiring a subsequent interferometric dataset from the film stack while the at least one laser beam is applied, wherein the subsequent interferometric dataset comprises a subsequent composite signal;
comparing the first composite signal to the subsequent composite signal;
determining a change in the thickness of the film stack based on the comparison, wherein a difference between the first composite signal and the subsequent composite signal indicates a change in the thickness of the film stack, and the change in the thickness of the film stack corresponds to a formation of bubbles at a retinal pigment epithelium of the eye; and
ceasing to apply the at least one laser beam to the film stack if the change in thickness of the film stack exceeds a predetermined threshold.

17. The dosimetry method of claim 16, wherein the film stack further comprises a contact lens placed on the eye, and wherein the tear film is a postlens tear film.

18. The dosimetry method of claim 16, wherein applying the at least one laser beam comprises using a laser treatment system.

19. The dosimetry method of claim 16, wherein the predetermined threshold is from about 3 nm to about 100 nm.

20. The dosimetry method of claim 16, wherein the predetermined threshold is configured to prevent damage caused by overheating.

\* \* \* \* \*